United States Patent [19]
Goulet

[11] Patent Number: 5,147,877
[45] Date of Patent: Sep. 15, 1992

[54] SEMI-SYNTHETIC IMMUNOSUPPRESSIVE MACROLIDES

[75] Inventor: Mark Goulet, Westfield, N.J.

[73] Assignee: Merck & Co. Inc., Rahway, N.J.

[21] Appl. No.: 759,746

[22] Filed: Sep. 12, 1991

Related U.S. Application Data

[63] Continuation of Ser. No. 687,366, Apr. 18, 1991, abandoned.

[51] Int. Cl.$^5$ ............... A61K 31/395; A61K 31/695; C07D 498/16
[52] U.S. Cl. .................................. 514/291; 514/183; 540/456
[58] Field of Search ................. 514/291, 183; 540/456

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,650,803 | 3/1987 | Stella et al. | 514/291 |
| 4,894,366 | 1/1990 | Okuhara et al. | 514/63 |
| 4,916,138 | 4/1990 | Ueda et al. | 514/294 |
| 4,929,611 | 5/1990 | Okuhara et al. | 514/183 |
| 4,956,352 | 9/1990 | Okuhara et al. | 514/63 |
| 4,986,382 | 9/1990 | Okuhara et al. | 314/291 |
| 4,987,139 | 1/1991 | Chen et al. | 514/321 |
| 5,011,844 | 4/1991 | Fehr | 514/291 |
| 5,057,608 | 10/1991 | Wyvratt, Jr. et al. | 540/456 |
| 5,064,835 | 11/1991 | Bochis et al. | 514/291 |

FOREIGN PATENT DOCUMENTS

| | | | |
|---|---|---|---|
| 0315978 | 5/1989 | European Pat. Off. | 514/291 |
| 0356399 | 2/1990 | European Pat. Off. | 514/291 |
| 0423714 | 4/1991 | European Pat. Off. | 514/291 |
| 0428169 | 5/1991 | European Pat. Off. | 514/291 |
| 0444659 | 9/1991 | European Pat. Off. | 514/291 |
| 0444829 | 9/1991 | European Pat. Off. | 514/291 |
| WO 90/14826 | 12/1990 | World Int. Prop. O. | 514/291 |

OTHER PUBLICATIONS

Tanaka et al., J. Am. Chem. Soc., 1987, 109 5031–5033.
Bierer et al., Science, 1990, 250, 556–559.
M. Goulet et al. (I) Tetrahedron Lett., 1991, 36, 4627.
C. Arita, et al., Clin. exp Immunol. 1990, 82, 456–461.
N. Murase et al., Diabetes, 1990, 39, 1584–1586.
J. McCauley et al., Lancet, 1990, 335, 674.
K. Takabayashi, et al., Clin. Immunol. Immunopathol., 1989, 51, 110–117.
M. Sakr, et al. Life Sciences, 1990, 47, 687–691.
D. Askin et al., (I) J. Org. Chem., 1990, 55, 5488–5450.
D. Askin, et al., (II) J. Org. Chem., 2990, 55, 5451–5454.
R. Coleman, et al., Heterocycles, 1989, 28, 157–161.
J. Findlay, et al., Can. J. Chem., 1980, 58, 579–590.
M. Goulet, et al. (II), Tetrahedron Lett., 1990, 31, 4845–4848.
T. Jones et al., J. Am. Chem. Soc., 1989, 111, 1157–1159.
S. Schreiber, Science, 1991, 251, 283–287.

*Primary Examiner*—Robert T. Bond
*Attorney, Agent, or Firm*—Charles M. Caruso; Robert J. North; J. Eric Thies

[57] ABSTRACT

Macrolides of the general structural Formula I:

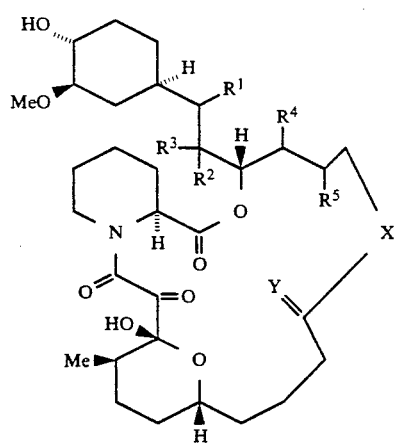

have been prepared. These macrolides are antagonists of FK-506-type immunosuppressants and are useful for modifying dosages of FK-506-type immunosuppressants in the treatment of autoimmune diseases, infectious diseases and/or the prevention of rejection of foreign organ transplants. Furthermore, the compounds of the present invention may have utility as antidotes for overdoses of FK-506-type immunosuppressants. In addition, these macrolide immunosuppressants are useful in a mammalian host for the treatment of autoimmune diseases, infectious diseases and/or the prevention of rejection of foreign organ transplants.

13 Claims, No Drawings

SEMI-SYNTHETIC IMMUNOSUPPRESSIVE MACROLIDES

This is a continuation of application Ser. No. 07/687,366, filed on Apr. 18, 1991 now abandoned.

SUMMARY OF THE INVENTION

The present invention is related to immunosuppressive macrolides which are useful in a mammalian host for the treatment and/or modification of treatment of autoimmune diseases (such as juvenile-onset diabetes mellitus, multiple sclerosis and rheumatoid arthritis), infectious diseases and/or the prevention of rejection of foreign organ transplants, e.g. bone marrow and heart transplants. In addition, the compounds of the present invention have antagonistic properties to FK-506-type immunosuppressants and so may be useful in the reversal of immunosuppressive activity or toxicity of FK-506-type immunosuppressive agents. In addition, they may also be useful in the topical treatment of inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, *Lichen planus*, Pemphigus, bullous Pemphigoid, *Epidermolysis bullosa*, urticaria, angioedemas, vasculitides, erythemas, cutaneous eosinophilias, *Lupus erythematosus* or *Alopecia areata*.

More particularly, this invention relates to compounds of the general structural Formula I:

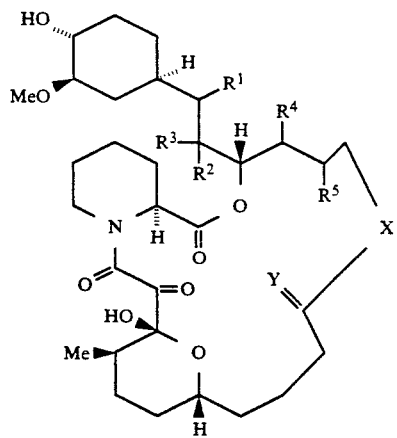

wherein $R^1$, $R^2$, $R^3$, $R^4$, $R^5$, X and Y are hereinafter defined.

This invention also relates to pharmaceutical compositions containing the compounds and to a method of use of the present compounds and other agents for the treatment and/or modification of treatment of autoimmune diseases, infectious diseases, the rejection of foreign organ transplants, inflammatory and hyperproliferative skin diseases and/or cutaneous manifestations of immunologically-mediated illnesses.

BRIEF DESCRIPTION OF DISCLOSURES IN THE ART

Rapamycin characterized by Findlay and co-workers in 1978 is a 35-membered macrolide isolated from *S. hygroscopicus* (*Can. J. Chem.*, 1978, 56, 2491, *J. Antibiotics*, 1975, 28, 721, U.S. Pat. No. 3,929,992, issued Dec. 30, 1975, U.S. Pat. No. 3,993,749, issued Nov. 23, 1975) and found to exhibit antifungal as well as modest immunomodulating behavior (*J. Antibiotics*, 1978, 31, 539; *J. Physiol. Pharmacol.* 1977, 55, 48; *Med. Sci. Res.*, 1989, 17, 877). Degradative studies of rapamycin have been conducted (*Can. J. Chem.*, 1980, 58, 579; *Tetrahedron Lett.*, 1990, 31, (4845), but the reassembly of the fragments obtained therefrom has not been reported.

Fujisawa United States, European and Japanese patents (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3-10,16-tetraone (FR-900506) (FK-506) (L-679-934), 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which have immunosuppressive activity similar to the compounds described. The synthetic preparation of the aforementioned starting material (FR-900506) has recently been reported (*J. Am. Chem. Soc.*, 1989, 111, 1157). A Fisons European patent (EPO Publication No. 0,323,042) discloses various derivatives of FR-900506, FR-900520 and related compounds. A Fujisawa United States patent (U.S. Pat. No. 4,929,611, issued May 29, 1990) discloses the use of FK-506-type compounds in treating resistance to transplantation. A Sandoz European patent (EPO Publication No. 0,315,978) discloses the use of FR-900506 and related compounds in the topical treatment of inflammatory and hyperproliferative skin diseases and of cutaneous manifestations of immunologically-mediated illness.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves opthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 35-membered tricyclo-macrolide rapamycin,

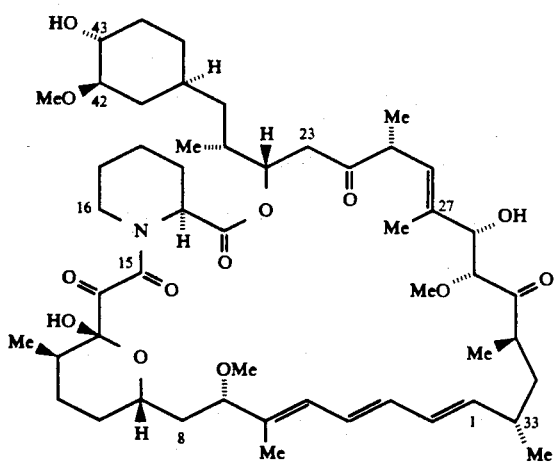

was isolated by Venza and co-workers. (*J. Antibiotics*, 1975, 28, 721) and characterized by Findlay and co-workers (*Can. J. Chem.*, 1978, 56, 2491). Rapamycin has been found to exhibit antifungal as well as modest immunomodulating behavior (*J. Antibiotics*, 1978, 31, 539; *Can. J. Physiol. Pharmacol.*, 1977, 55, 48; *Med. Sci. Res.*, 1989, 17, 877).

Prior studies on the degradation of rapamycin have been conducted (M. T. Goulet, et al., *Tetrahedron Lett.*, 1990, 31, 4845–4848; J. A. Findlay, et al., *Can. J. Chem.*, 1980, 58, 579). The reassembly of such fragments, however, has not been reported.

The 23-membered tricyclo-macrolide immunosuppressant, FR-900506, (FK-506), (L-679,934),

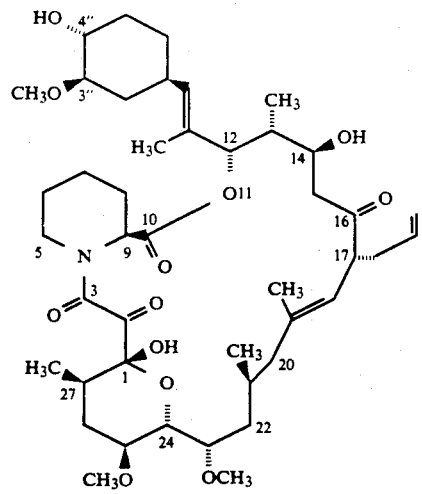

and related compounds which were isolated and characterized by Tanaka, Kuroda, and co-workers at Fujisawa Pharmaceutical Co. in Japan (see *J. Am. Chem. Soc.*, 1987, 109, 5031, and U.S. Pat. No. 4,894,366, issued Jan. 16, 1990) have been shown to possess exceptional immunosuppressive activity. A Fujisawa United States patent (U.S. Pat. No. 4,929,611, issued May 29, 1990) discloses the use of FK-506-type compounds in treating resistance to transplantation. In particular, the compound FR-900506 has been reported to be 100 times more effective than cyclosporin in the suppression of in vitro immune systems (*J. Antibiotics*, 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978). Although FR-900506 is a potent immunosuppressant, it also exhibits toxic side effects.

The compound FK-506 and related compounds further have been suggested to be useful in the treatment of obstructive airways disease, particularly asthma (PCT Publication WO 90/14826), rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al. *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K. Deguchi, et al., *Brain Nerve*, 1990, 42, 391–97), glomerulonephritis (J. McCauley, et al., *Lancet*, 1990, 335, 674) and systemic lupus erythematosus (K. Takabayashi, et al., *Clin. Immunol. Immunopathol.*, 1989, 51, 110–117).

Studies on the degradation of FK-506 have been conducted (*J. Org. Chem.*, 1987, 109, 5031; *J. Org. Chem.*, 1990, 55, 5451; *Heterocycles*, 1989, 28, 157; *J. Org. Chem.*, 1989, 54, 11,). The reassembly of fragments derived from FK-506 has been examined (*J. Org. Chem.*, 1990, 55, 5448). Compounds containing common structural features of FK-506 and rapamycin have been prepared by total synthesis (*Science*, 1990, 250, 556).

The striking structural similarity of rapamycin to the immunosuppressant FK-506 makes the former an attractive alternate source of material for semi-synthetic efforts in this area.

Accordingly, an object of the present invention is to provide new analogs of these tricyclomacrolides which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide new analogs of these tricyclomacrolides which will (1) modify the restoration of the balance of the help-and-suppression mechanism of the immune system with macrolide immunosuppressants and (2) modify the induction of transplantation tolerance by macrolide immunosuppressants.

An additional object of the present invention is to provide new analogs of these tricyclomacrolide immunosuppressants which have antagonistic properties. These analogs would find utility in the reversal of the immunosuppressive activity of other FK-506-type immunosuppressive agents and so provide antidotes for overdoses of the immunosuppressants.

Another object of the present invention is to provide analogs of these tricyclo-macrolides which possess topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory dieases by administering a sufficient amount of one or more of the novel immunosuppressive agents in a mammalian species in need of such treatment and to provide a method of modifying the activity of FK-506-type immunosuppressants (which are utilized in controlling graft rejection, autoimmune and chronic inflammatory diseases) by administering a sufficient amount of one or more of the novel macrolide immunosuppressive antagonists in a mammalian species in need of such treatment.

Finally, it is the object of this invention to provide processes for the preparation of the active compounds of the present invention.

DETAILED DESCRIPTION OF THE INVENTION

A. Scope of the Invention

The novel compound of this invention has structural Formula I:

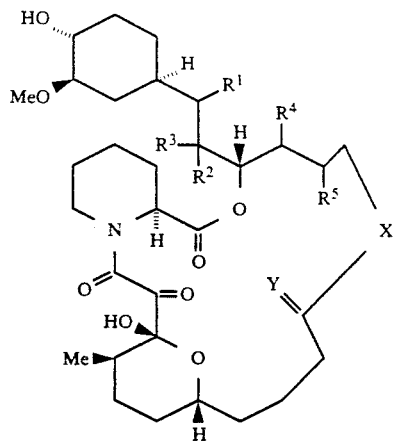

or a pharmaceutically acceptable salt thereof, wherein:
X is selected from:

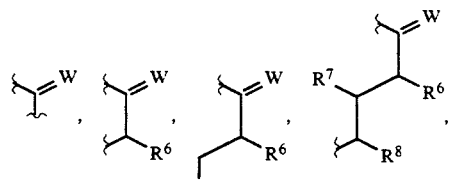

or forms a single bond;
W is O, (H, OH) or (H, H);
Y is O, (H, OH), or (H, H);
$R^1$ and $R^2$ are hydrogen or taken together form a double bond;
$R^3$ is hydrogen or methyl;
$R^4$ is selected from:
  (1) hydrogen, or
  (2) $C_{1-6}$ alkyl, unsubstituted or substituted with one or more of:
    (a) $C_{1-6}$ alkoxy,
    (b) phenyl, unsubstituted or substituted with $C_{1-6}$ alkyl,
$R^5$ is hydrogen or hydroxy;
$R^6$ is selected from:
  (1) hydrogen;
  (2) $C_{1-6}$ alkyl, unsubstituted or substituted with one or more of:
    (a) $C_{1-6}$ alkoxy,
    (b) phenyl, unsubstituted or substituted with $C_{1-6}$ alkyl,
  (3) $C_{2-6}$ alkenyl; and
$R^7$ and $R^8$ are hydrogen or taken together form a double bond.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, $R^6$, $R^7$, $R^8$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. As used herein the term "agonist" denotes ability to initiate or promote a particular drug activity. The term "antagonist" denotes the ability to block a particular drug activity.

In the present invention it is preferred that in compounds of Formula I:

X is selected from:

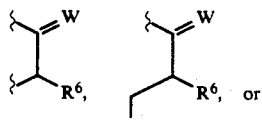

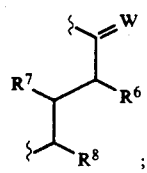

W is (H, H);
Y is O;
$R^1$ and $R^2$ are hydrogen;
$R^3$ is hydrogen or methyl;
$R^4$ is selected from:
  (1) hydrogen, or
  (2) unsubstituted $C_{1-6}$ alkyl;
$R^5$ is hydrogen or hydroxy;
$R^6$ is hydrogen; and
$R^7$ and $R^8$ are hydrogen.
and pharmaceutically acceptable salts thereof.

Preferred compounds of the present invention are the compounds identified as follows:

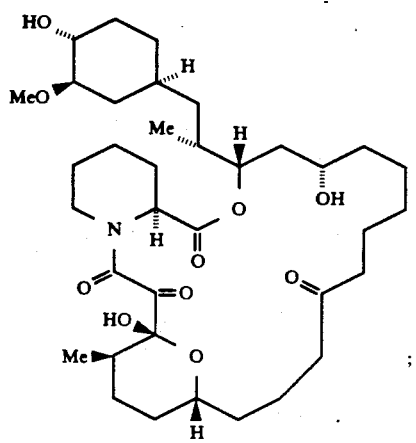

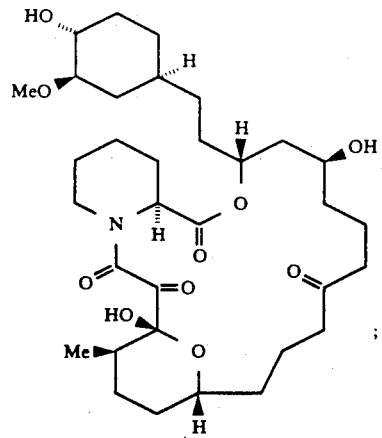

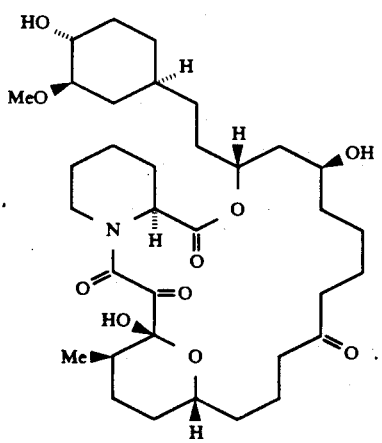

B. Preparation of Compounds Within the Scope of the Present Invention

The starting materials for the preparation of the compounds of this invention are represented by Formulas II and III:

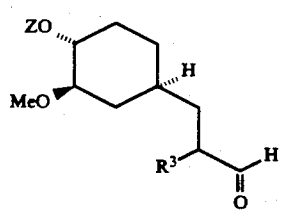

and

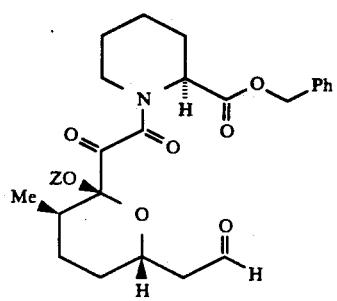

Wherein Z is independently hydrogen or a hydroxyl protecting group selected from:
trisubstituted silyl such as tri(lower)alkylsilyl (e.g. trimethylsilyl, triethylsilyl, tributylsilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri-($C_1$–$C_4$)alkylsilyl and $C_1$–$C_4$ alkyl-diphenylsilyl, and the most preferred one may be tert-butyl-dimethylsilyl, tri-i-propylsilyl and tert-butyl-diphenylsilyl and $R^3$ is as defined above.

Compounds of Formulas I and II may be prepared by degradation of the macrolide:

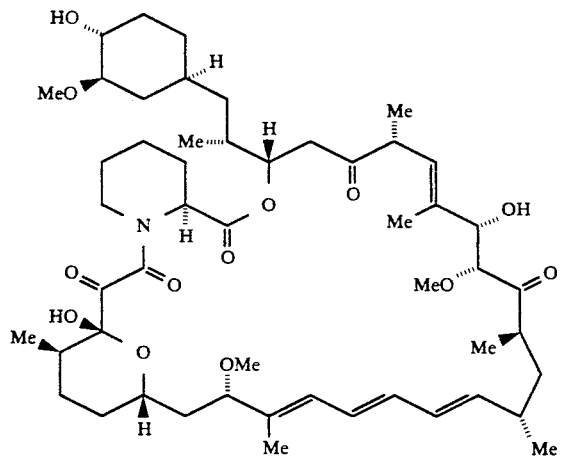

essentially by methods described in *Tetrahedron Lett.*, 1990, 34, 4845.

These may also be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *J. Org. Chem.*, 1990, 55, 5448; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287). In particular, compounds of Formula III may be prepared essentially by procedures described in *J. Org. Chem.* 1988, 53, 4643; *Tetrahedron Lett.* 1988, 29, 4481; *Tetrahedron Lett.* 1989, 30, 919; *J. Org. Chem.*, 1989, 54, 11; *J. Org. Chem.* 1989, 54, 2785; or *Tetrahedron Lett.* 1990, 31, 1439.

The novel processes for preparing the novel compounds of the present invention are illustrated as follows, wherein $R^1$, $R^2$, $R^3$, $R^4$, $R^5$, and X are as defined above unless otherwise indicated.

REACTION SCHEME A

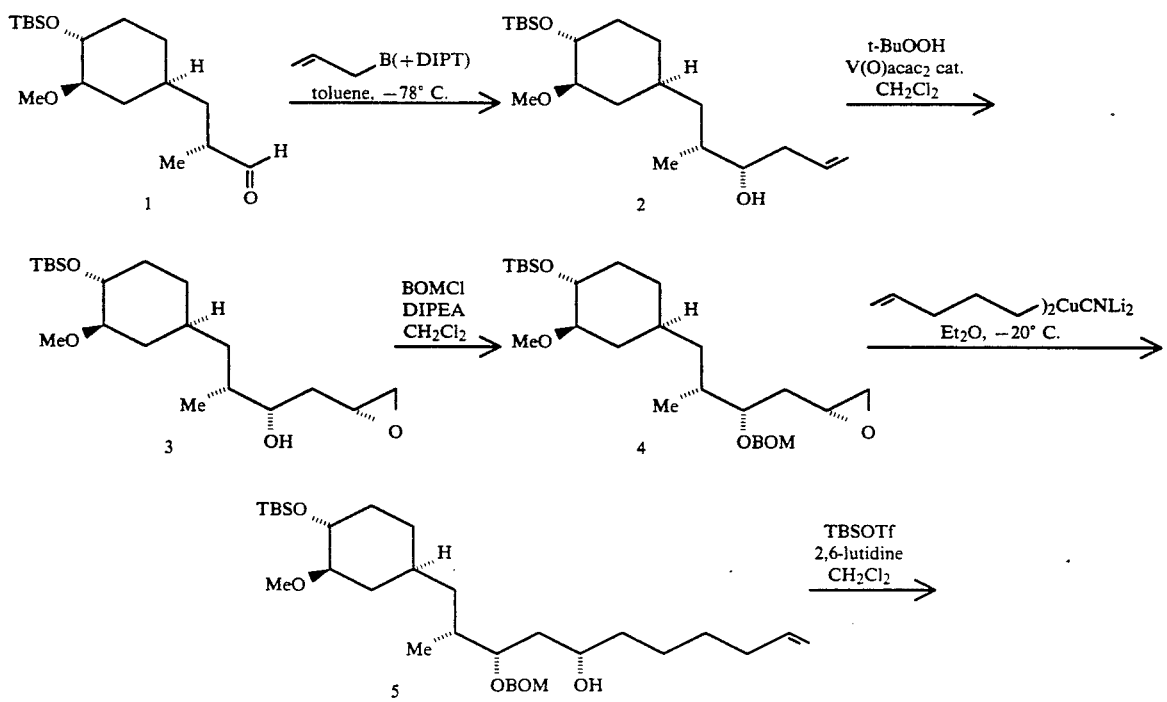

5,147,877
-continued
REACTION SCHEME A
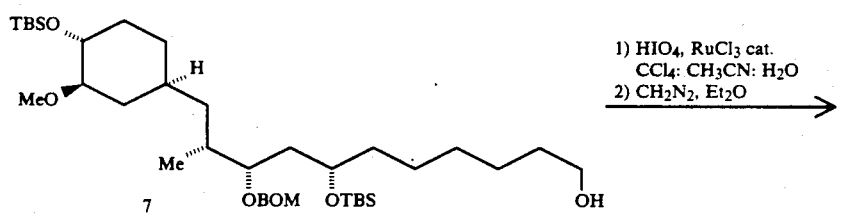
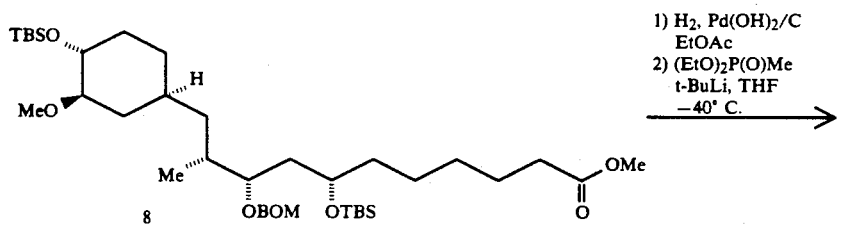
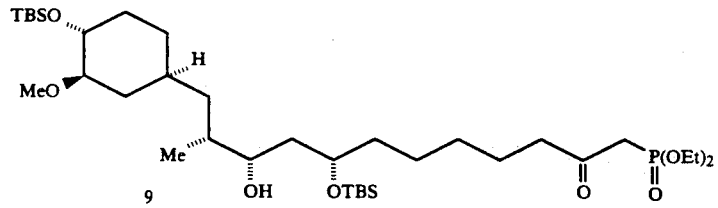
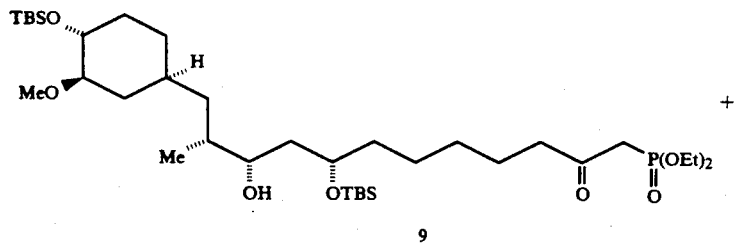
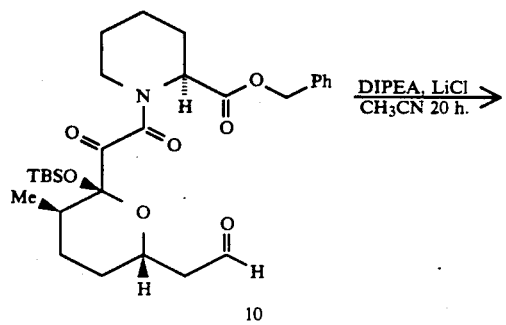

-continued
REACTION SCHEME A

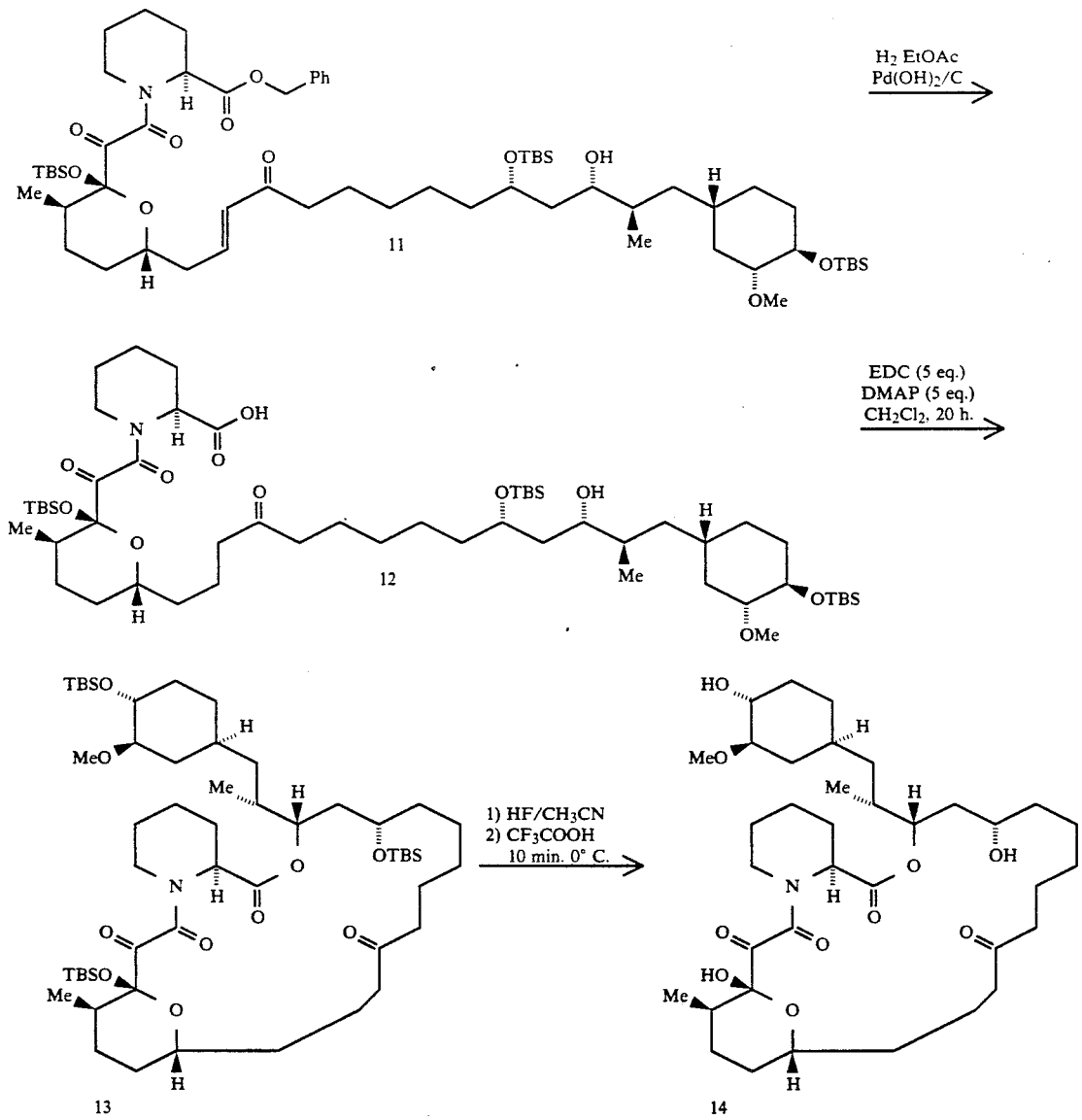

As shown in the reaction Scheme 1, aldehyde 1 (prepared as described in Goulet, M. T.; Boger, J. *Tetrahedron Lett.* 1990, 31, 4845) in an inert organic solvent such as toluene is treated with a disopropyl tartrate-modified allyl boronate at about −78° C. for a period of one to twelve hours to give the homoallylic alcohol 2 with a high degree of diastereoselection. Epoxidation of the olefin contained in 2 is conducted by treatment of a solution 2 in an inert organic solvent such as benzene, toluene, methylene chloride, or tetrahydrofuran with an alkyl hydroperoxide such as tertbutyl hydroperoxide and a catalytic amount of vanadyl acetylacetonate at room temperature for a period of ten to twenty-four hours to give the cis epoxy-alcohol 3 as the major product. Alcohol 3 is protected as the benzyloxymethyl ether by treatment of a methylene chloride solution with benzyl chloromethyl ether and an amine base such as diisopropylethyl amine or triethylamine at room temperature for a period of ten to twenty-four hours to give the protected analog 4. The extended alcohol 5 is prepared by subjection of a solution of epoxide 4 in an inert organic solvent such as diethyl ether or tetrahydrofuran to the cyanocuprate prepared from 4-pentenyl lithium at about −20° C. for one to three hours. Alcohol 5 is protected as the tert-butyldimethylsilyl ether by subjection of a solution in methylene chloride to tert-butyldimethylsilyl trifluoromethanesulfonate and an amine base such as 2,6-lutidine at room temperature for fifteen minutes to one hour giving the protected derivative 6. Selective hydroboration of olefin 6 to the primary alcohol 7 is accomplished by treatment of a solution of 6 in ethylene glycol dimethyl ether with 9-borabicyclo[3.3.1]nonane a 0° C. for a period of one to eight hours, followed by addition of saturated sodium bicarbonate and hydrogen peroxide. This mixture is stirred at room temperature for thirty minutes to two hours to give alcohol 7. Treatment of alcohol 7 as a mixed solution in carbon tetrachloride, acetonitrile, and water with periodic acid and a catalytic amount of ruthenium (III) chloride at room temperature for two to five hours, followed by treatment of the crude reaction product with diazomethane in ether gives methyl ester 8. The benzyloxymethyl ether protecting group is removed from 8 by treatment of an ethyl acetate solution with hydrogen and a catalytic amount of palladium hydroxide on carbon to produce the free alcohol. Treatment of this crude product with an excess of the lithium anion of methyl diethylphosphonate in tetrahydrofuran at −40° C. for a period of thirty minutes to two hours is followed by acidification with a weak acid such as aqueous ammonium chloride to give the β-keto-phosphonate 9.

Phosphonate 9 is coupled with aldehyde 10 (prepared as described in *Tetrahedron Lett.* 1990, 31, 4845) by treatment of a dry acetonitrile solution of these compounds with lithium chloride and an amine base such as triethylamine or diisopropylethyl amine at or near room temperature for twenty to thirty-six hours to give the enone 11. The benzyl group of 11 is removed with concomitant olefin reduction by treatment of an ethyl acetate solution with hydrogen and a catalytic amount of palladium hydroxide on carbon catalyst followed by acidification with an organic acid such as acetic acid to give the saturated carboxylic acid 12. Cyclization of the hydroxy-acid 12 is effected by treatment of a dilute methylene chloride solution with dimethylaminopyridine and 1-ethyl-3-(3-dimethylamino)propylcarbodiimide for a period of five to twenty-four hours to give the macrolide 13. Deprotection of 13 is conducted by first treating an acetonitrile solution of the tris(silyl) ether) 13 with a 2% solution of hydrogen fluoride in aqueous acetonitrile at room temperature for one to three hours, followed by neutralization with saturated sodium bicarbonate. The mono(silyl) ether thus obtained is then solvated in trifluoroacetic acid at 0° C. and stirred for a period of ten to thirty minutes after which time it is concentrated in vacuo at 0° C. and the remaining acid neutralized by addition of aqueous saturated sodium bicarbonate to give the fully deprotected macrocycle 14.

REACTION SCHEME B

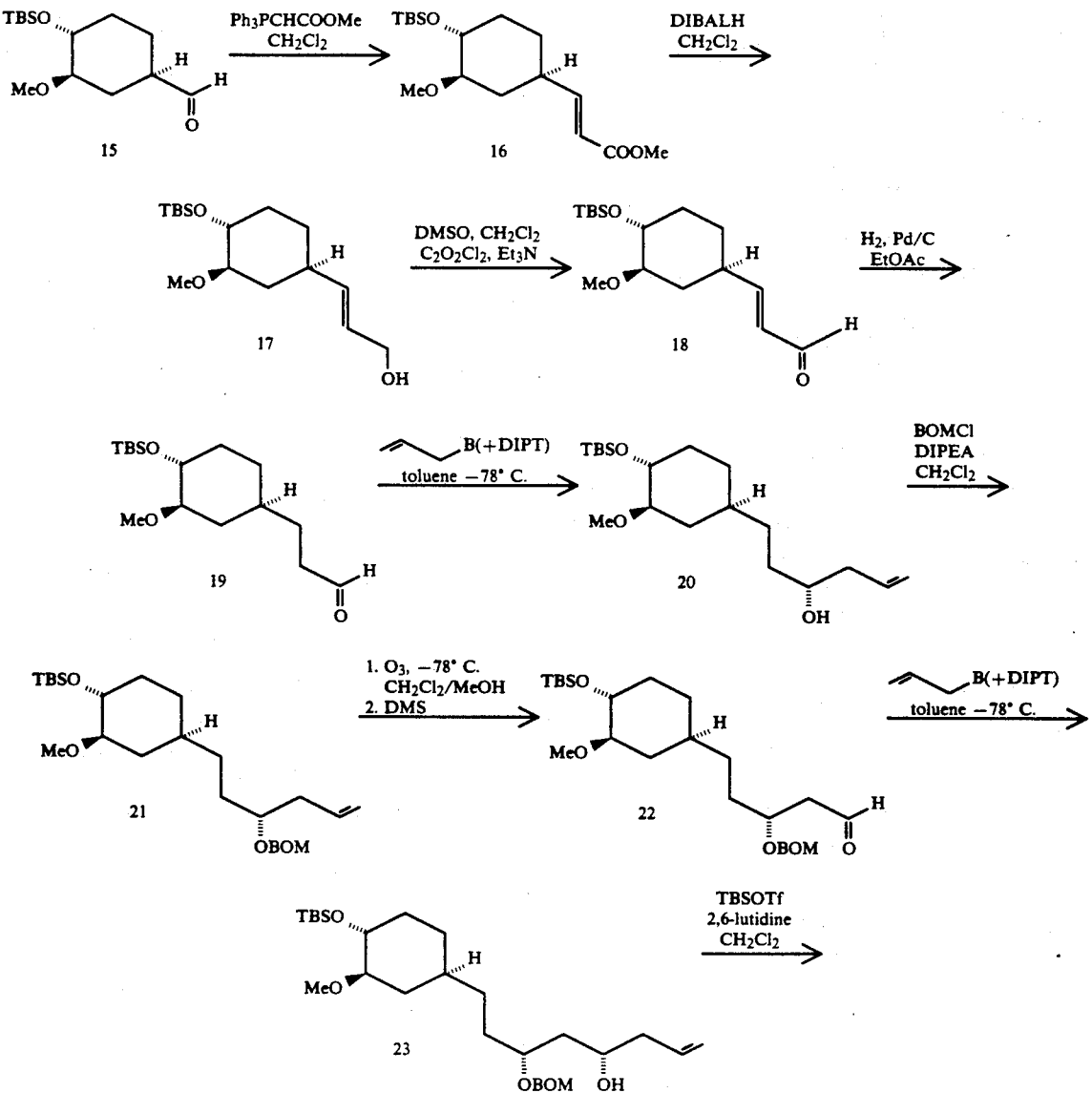

-continued
REACTION SCHEME B
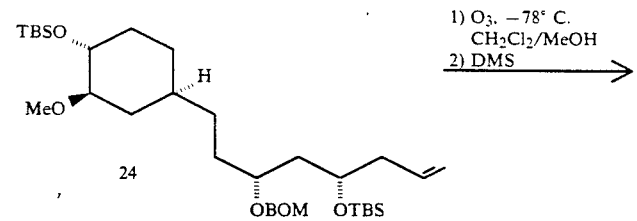
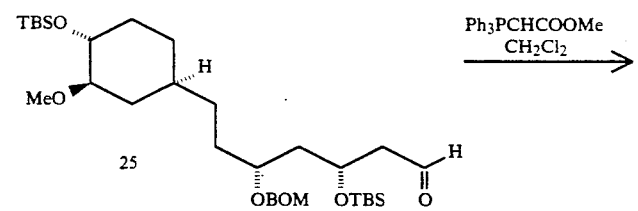
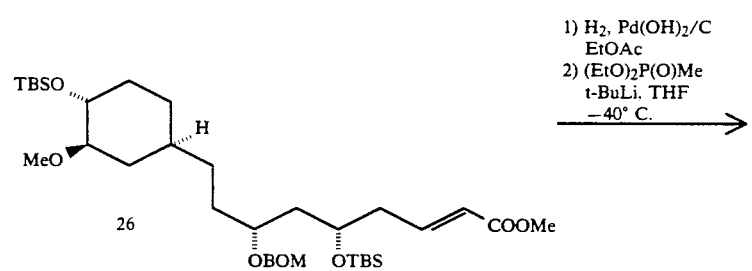
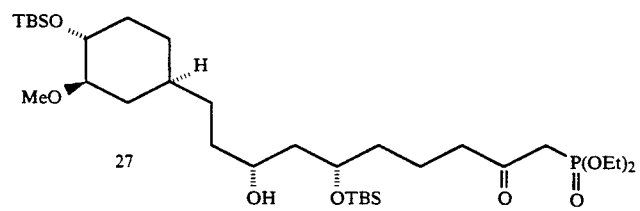
+
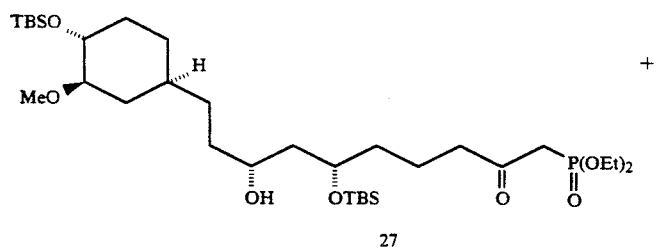
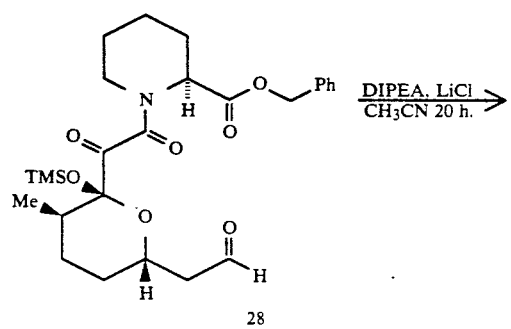

-continued
REACTION SCHEME B

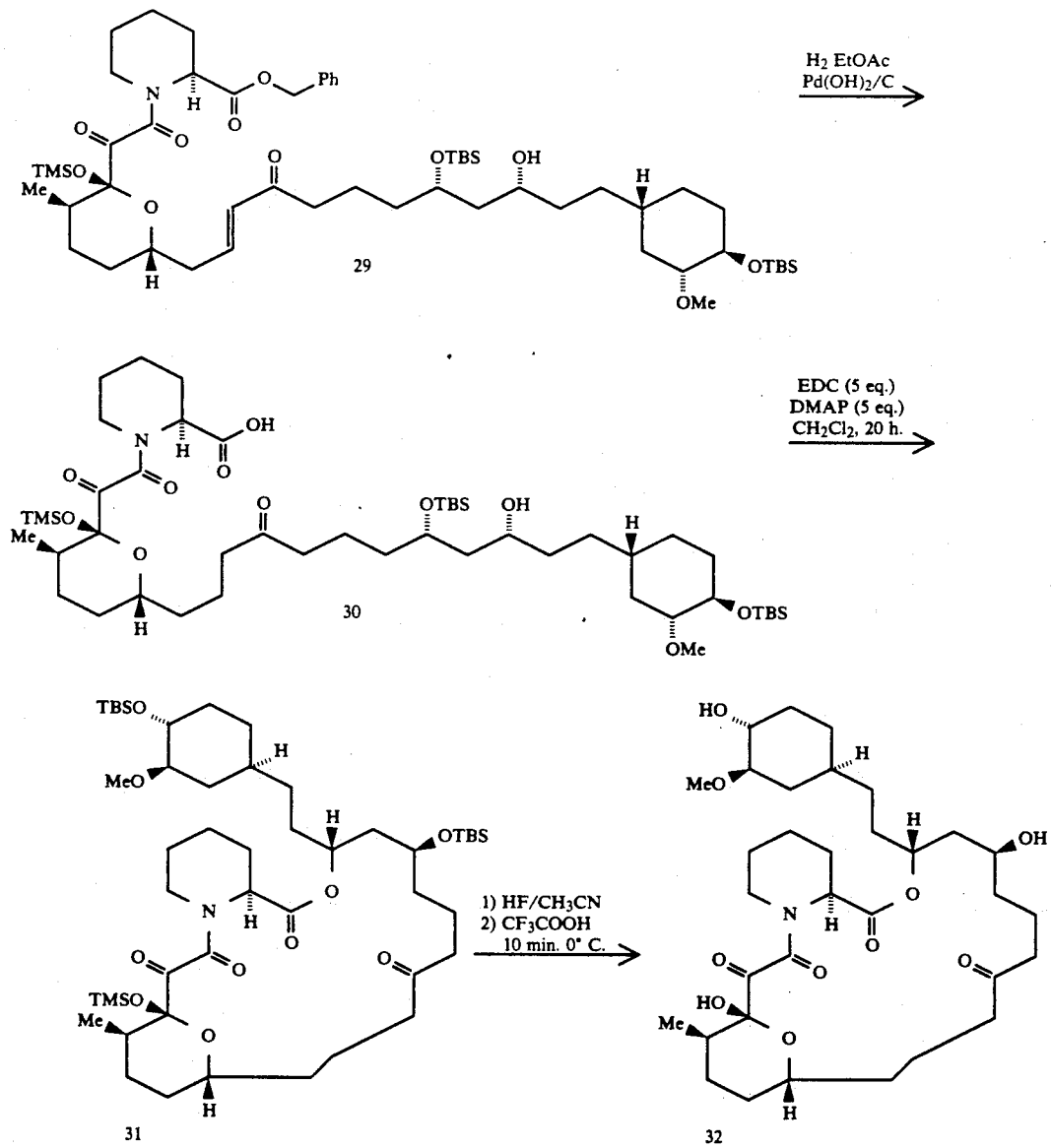

As shown in Reaction Scheme B, a solution of aldehyde 15 (prepared as described in *Tetrahderon Lett.*, 1990, 31, 3287) is reacted with an appropriate Wittig reagent to give the unsaturated ester 16. Reduction of the ester with diisobutylaluminum hydride gives the alcohol 17, which is oxidized to the unsaturated aldehyde 18 under Swern conditions. Catalytic hydrogenation to 19 followed by treatment with a diisopropyl tartrate-modified allyl boronate gives the homoallylic alcohol 20. Protection as the benzyloxymethyl ether followed by ozonolysis gives the aldehyde 22. Treatment with a diisopropyl tartrate-modified allyl boronate gives the homoallylic alcohol 23. Protection of the alcohol as the tert-butyl dimethylsilyl ether followed by ozonolysis gives the protected dihydroxy aldehyde 25. The aldehyde 25 is coupled with appropriate Wittig reagent to give the unsaturated ester 26. Catalytic hydrogenation followed by treatment with diethyl methylphosphonate and deprotonation gives the Wittig reagent 27.

The Wittig reagent 27 is coupled with aldehyde 28 (prepared essentially as described in *Tetrahedron Lett.*, 1990, 31, 4845) to give 29. Catalytic reduction followed by macrolactonization with EDC gives the cyclic 31. Removal of the hydroxyl protecting groups yields the macrolide 32.

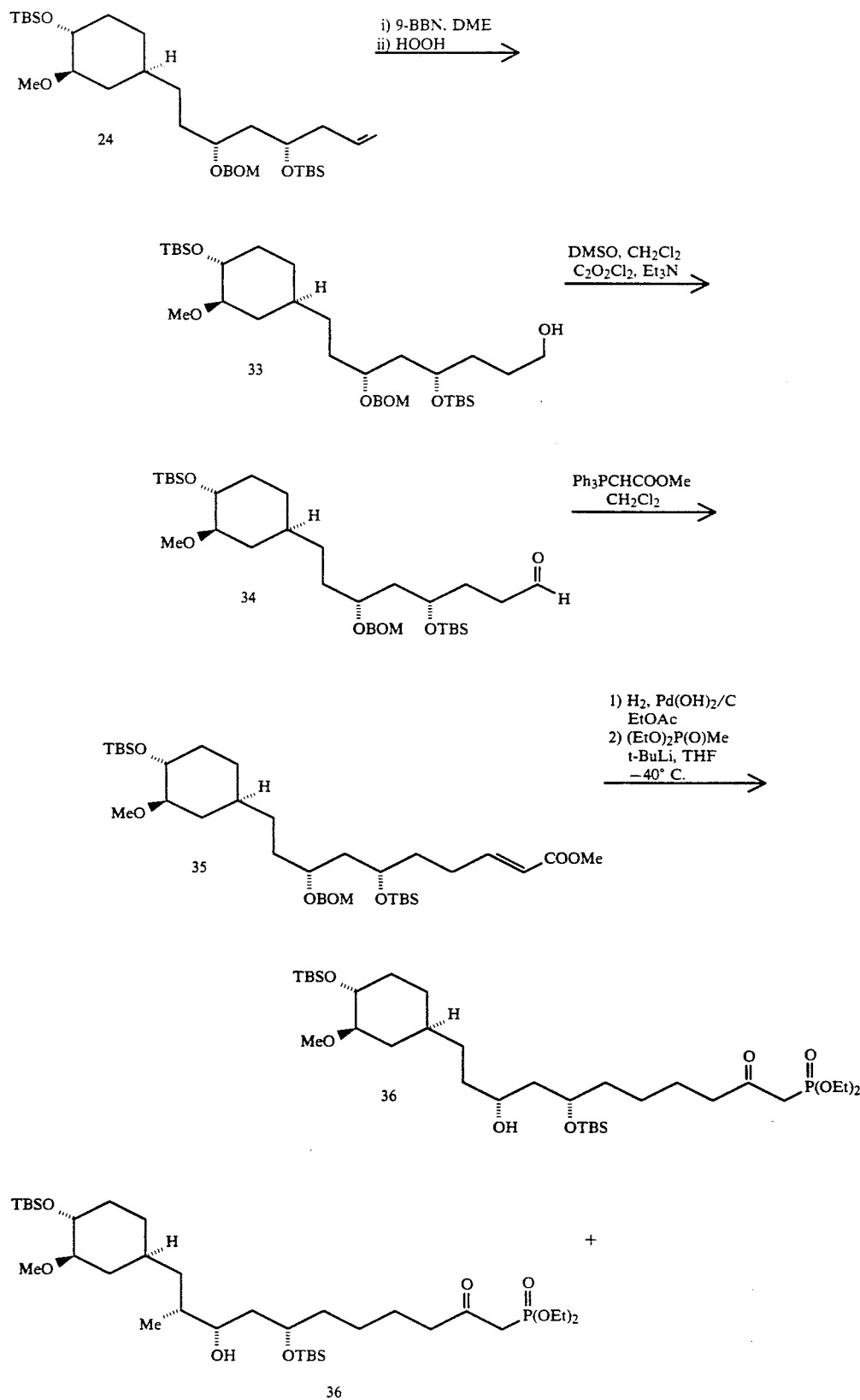
REACTION SCHEME C

-continued
REACTION SCHEME C

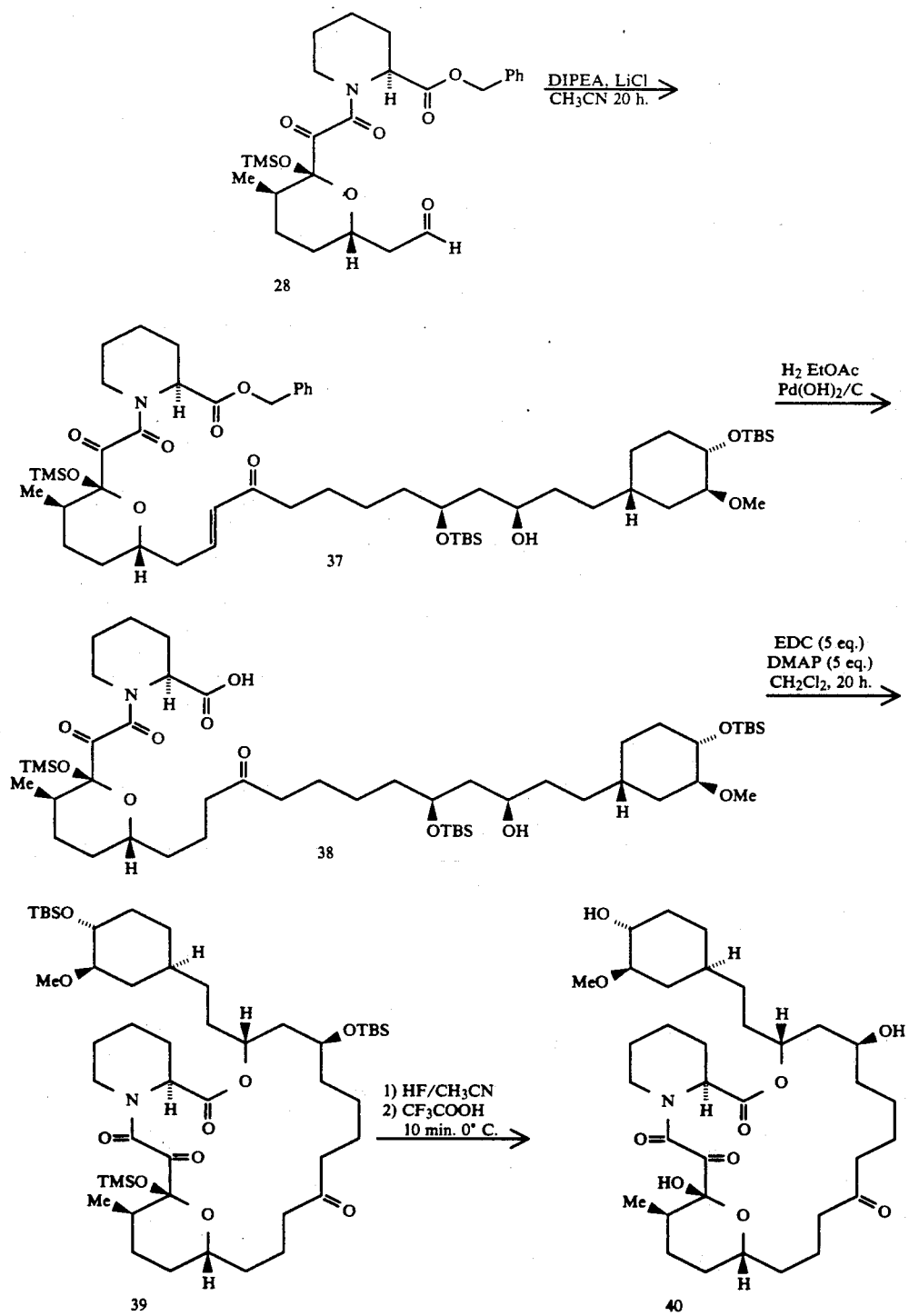

As shown in Reaction Scheme C, the olefin 24 (from Reaction Scheme B) is converted to the alcohol 33 by hydroboration. Swern oxidation to the aldehyde 34 followed by reaction with an appropriate Wittig reagent gives the unsaturated ester 35. Subsequent reaction under conditions essentially identical to those described in Reaction Scheme A and B, ultimately gives the macrolide 40.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by variations of methods described herein.

C. Utility of the Compounds Within the Scope of the Invention

The compounds of Formula I may be employed as immunosuppressants or antimicrobial compounds or as antagonists of FK-506-type immunosuppressants by methods and in dosages known in the prior art for FK-506-type compounds. These compounds possess pharmacological activity such as immunosuppressive activity, antimicrobial activity, antagonism of immunosuppressive activity, and the like, and therefore are useful for the treatment or the modification of the treatment of the resistance to transplantation or transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms. The compounds of Formula I may also be useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, *Lichen planus*, Pemphigus, bullous Pemphigoid, *Epidermolysis bullosa*, urticaria, angioedemas, vasculitides, erythemas, cutaneous eosinophilias or *Alopecia areata*.

The compounds of Formula I may be further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyperresponsiveness), bronchitis and the like. The compounds of Formula I may also be useful for treating hepatic injury associated with ischemia. In addition, the compounds of Formula I have antagonistic properties and so may have utility in the reversal of immunosuppressive activity of other FK-506-type immunosuppressive agents and/or in diminishing their toxic effects.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

This invention also relates to a method for the treatment or the modification of the treatment of patients suffering from immunoregulatory abnormalities involving the administration of a compound of Formula I as the active constituent.

For the treatment of immunoregulatory disorders or the modification of the treatment with FK-506-type immunosuppressants of these conditions and diseases caused by immunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. For applying a composition of this invention to a human, it is preferable to apply it by parenteral or oral administration.

Dosage levels of the compounds of the present invention of the order from about 0.01 mg to about 50 mg per kilogram of body weight per day, preferably from about 0.1 mg to about 10 mg per kiolgram body weight per day, are useful in the treatment of the above-indicated conditions (from about 0.7 mg to about 3.5 gm per patient per day, assuming a 70 kg patient). In addition, the compounds of the present invention may be administered on an intermittent basis; i.e. at semiweekly, weekly, semimonthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 1 gm of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1–3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

The compounds 1, 10, 15, 24 and 28 may be obtained essentially as described in *Tetrahedron Lett*. 1990, 31, 4845 or as described in *Tetrahedron Lett*. 1990, 31, 3287.

EXAMPLE 2

To a −78° C. solution of 1 (88 mg in 2.0 ml toluene; prepared as described in *Tetrahedron Lett*. 1990, 31, 4845) was added 25 mg of powdered, 4A molecular sieves and diisopropyl-L-tartrate modified allylboronate (650 μl of a 15% toluene solution), and the mixture stirred at low temperature. After 15 minutes, an additional 400 μl of reagent were added. The mixture was quenched by the addition of saturated sodium bicarbonate solution after 1 hour reaction time. This was then diluted with ether, extracted, and dried over magnesium sulfate. Purification by flash chromatography on silica gel (ethyl acetate:hexane 1:8) gave 2 (46 mg).

Partial $^1$H NMR δ: 5.69(m, 1H); 5.11(brd J=14 Hz, 2H); 3.38(m, 2H); 3.36(s, 3H); 2.85(m, 1H); 0.87 (d J=5 Hz, 3H); 0.84(s, 9H); 0.03(s, 3H); 0.01(s, 3H).

EXAMPLE 3

To a solution of the product of Example 2 (134 mg in 4.0 ml methylene chloride) was added vanadyl acetylacetonate (11.3 mg) and the mixture stirred at room temperature. After 15 minutes, tert-butyl hydroperoxide (213 μl of a 3M solution in 2,2,4-trimethylpentane) was added. The mixture was quenched after 16 hours by addition of a 10% sodium sulfite solution. This was extracted with ethyl acetate, washed with brine, and the organic portion dried over magnesium sulfate. The concentrate was purified by flash chromatography on silica gel (ethyl acetate:hexane 1:4) to give 3 as a 4:1 mixture of diastereomers (63 mg).

Partial $^1$H NMR δ: 3.73(m, 1H); 3.35(m, 1H); 3.39(s, 3H); 2.87(m, 1H); 2.79(dd J=4, 4 Hz, 1H); 2.48(dd J=4, 3 Hz, 1H); 0.87(d J=5 Hz, 3H); 0.84(s, 9H); 0.03(s, 3H); 0.01(s, 3H).

EXAMPLE 4

To a solution of the product of Example 3 (365 mg in 7.0 ml methylene chloride) was added diisopropylethyl amine (683 μl) followed by benzyl chloromethyl ether (273 μl), and the mixture heated to reflux on a mantle. After 18 hours, the reaction mixture was cooled and poured into saturated sodium bicarbonate. The layers were separated and the aqueous portion extracted with ethyl acetate. The combined organics were washed with brine, dried over magnesium sulfate and concentrated in vacuo. Purification by flash chromatography on silica gel (ethyl acetate:hexane 1:4) gave 4 (390 mg).

Partial $^1$H NMR δ: 7.35(m, 5H); 4.82(s, 2H); 4.64 (s, 2H); 3.68(m, 1H); 3.40(s, 3H); 3.38(m, 1H); 2.87(m, 1H); 2.75(dd J=4, 4 Hz, 1H); 2.46(dd J=4, 3 Hz, 1H).

EXAMPLE 5

To a suspension of copper (I) cyanide (44 mg in 1.0 ml ether) at −40° C. was added 4-pentenyllithium (13 ml of a 0.075M solution in ether) and the mixture stirred for 30 minutes. At this time, a solution of the product of Example 4 (146 mg in 0.5 ml ether) was added dropwise via syringe. After 1 hour the reaction was warmed to 0° C. then quenched by the addition of a saturated ammonium chloride:ammonium hydroxide (95:5) solution. The mixture was extracted with ether and dried over magnesium sulfate. Purification of the concentrate by flash chromatography on silica gel (ethyl acetate:hexane 1:5) gave 5 as a single diastereomer (53 mg).

Partial $^1$H NMR δ: 7.35(m, 5H); 5.83(m, 1H); 3.75 (m, 2H); 3.50(s, 3H); 3.25(brs, 1H); 2.88(m, 1H).

EXAMPLE 6

To a solution of the product of Example 5 (220 mg in 4.0 ml methylene chloride) was added 2,6-lutidine (123 μl) followed by tert-butyldimethylsilyl trifluoromethanesulfonate (117 μl) and the mixture stirred at room temperature. After 15 minutes, the reaction was quenched by the addition of saturated sodium bicarbonate. This was extracted with ethyl acetate:hexane (3:1), and the organic portion dried over magnesium sulfate. Purification of the concentrate by flash chromatography on silica gel (ethyl acetate:hexane 1:10) gave 6 (283 mg).

Partial $^1$H NMR δ: 7.35(m, 5H); 5.81(m, 1H); 3.81 (m, 1H); 3.57(m, 1H); 3.39(s, 3H); 2.87(m, 1H).

EXAMPLE 7

To a 0° C. solution of the product of Example 6 (75 mg in 1.0 ml ethylene glycol dimethyl ether) was added 9-borabicyclo[3.3.1]nonane (9-BBN, 345 μl of a 0.5M solution in tetrahydrofuran) and the mixture warmed to room temperature. After 15 minutes, an additional 100 μl of 9-BBN was added. The reaction was quenched after 1 hour by addition of half-saturated sodium bicarbonate, dilution with ether, and addition of 100 μl of 30% hydrogen peroxide. This was stirred vigorously for 30 minutes at which time the layers were separated and the aqueous portion washed with 10% sodium sulfite then extracted with ethyl acetate. The combined organics were dried over magnesium sulfate and concentrated in vacuo. Purification by flash chromatography on silica gel (ethyl acetate:hexane 1:4) gave 7 (55 mg).

Partial $^1$H NMR δ: 7.35(m, 5H); 4.77(dd J=12, 9 Hz, 2H); 4.65(s, 2H); 3.82(m, 2H); 3.61(m, 2H); 3.42 (s, 3H); 2.90(m, 1H).

EXAMPLE 8

To a rapidly stirred suspension of ruthenium (III) chloride (4 mg) and periodic acid (112 mg, in 750 μl carbon tetrachloride:acetonitrile (1:1)+2 ml distilled water) at 0° C. was added a solution of the product of Example 7 (153 mg in 250 μl carbon tetrachloride:acetonitrile (1:1)). This was warmed to room temperature and stirred for 2.5 hours after which time it was quenched by the addition of 200 μl isopropanol and filtered through diatomaceous earth. The filtrate was extracted with ethyl acetate, washed with brine, and dried over magnesium sulfate. The crude acid was solvated in 800 μl ether and treated with excess diazomethane. After the gas evolution had ceased, an excess of acetic acid was added and the now colorless solution concentrated in vacuo. Purification by flash chromatography on silica gel (ethyl acetate:hexane 1:12) gave 8 (94 mg).

Partial $^1$H NMR δ: 7.35(m, 5H); 4.78(12, 9 Hz, 2H); 4.64(s, 2H); 3.83(m, 1H); 3.68(s, 3H); 3.78(m, 1H); 3.40(s, 3H); 2.88(m, 1H); 2.33(t J=7 Hz, 2H).

EXAMPLE 9

To a solution of the product of Example 8 (26 mg in 1.0 ml ethyl acetate) was added 5 mg of 20% palladium hydroxide on carbon catalyst. The reaction flask was fitted with a hydrogen balloon, evacuated and recharged with hydrogen (3 times) and stirred at room temperature. After 2.5 hours, the mixture was filtered over diatomaceous earth, concentrated, and purified by passage through a small silica gel column (ethyl acetate:hexane 1:1). This product was added directly (14 mg in 100 μl tetrahydrofuran) to a solution of the anion of methyl diethylphosphonate (prepared by mixing methyl diethylphosphonate, 22.8 mg, with tert-butyllithium, 176 μl of a 0.85M solution, in 150 μl of tetrahydrofuran at −40° C. for 30 minutes). The reaction is quenched after 30 minutes by addition of saturated ammonium chloride and extracted with ether. The combined organics were dried over magnesium sulfate, and the concentrate purified by flash chromatography on silica gel (ethyl acetate:hexane (1:1)+1% methanol) to give 9 (8 mg).

Partial $^1$H NMR δ: 4.18(dq J=9, 8 Hz, 4H); 3.92(m, 1H); 3.59(m, 1H); 3.43(s, 3H); 3.18(brs, 1H); 3.08(d J=24 Hz, 2H); 2.92(m, 1H); 2.66(t J=7 Hz, 2H); 1.38(t J=8 Hz, 6H).

EXAMPLE 10

To a solution of β-keto phosphonate 9 (7.8 mg in 150 μl dry acetonitrile) was added lithium chloride (2.0 mg) and diisopropylethylamine (6.0 μl) and the suspension stirred at room temperature. After 15 minutes, a solution of aldehyde 10 (10.8 mg in 150 μl acetonitrile; prepared as described in: Goulet, M. T.; Boger, J. *Tetrahedron Lett.* 1990, 31, 4845) was added. The reaction was quenched after 16 hours by addition of saturated ammonium chloride, extracted with ethyl acetate, and dried by passage through a magnesium sulfate plug. Purification of the concentrate by flash chromatography on silica gel (ethyl acetate:hexane (1:2)+1% methanol) gave 11 (9.5 mg).

Partial $^1$H NMR δ: 7.36(m, 5H); 6.78(dt J=14, 6 Hz, 1H); 6.11(d J=14 Hz, 1H); 4.72(brs, 1H); 3.40(s, 3H); 3.11(s, 1H); 2.90(m, 1H); 2.49(t J=7 Hz, 2H).

EXAMPLE 11

To a solution of 11 (9.5 mg in 1.0 ml ethyl acetate) was added 5 mg of 20% palladium hydroxide on carbon catalyst. The reaction flask was fitted with a hydrogen balloon, evacuated and recharged with hydrogen (3 times) and stirred at room temperature. After 2 hours, the mixture was filtered over diatomaceous earth, concentrated, and purified by passage through a small silica gel column (ethyl acetate+1% acetic acid) to give 12 (5 mg).

Partial $^1$H NMR δ: 3.92(m, 2H); 3.62(m, 1H); 3.44 (s, 3H); 2.94(m, 1H).

EXAMPLE 12

To a solution of the seco-acid 12 (10 mg in 1.95 ml methylene chloride) was added a mixture of dimethylaminopyridine (6 mg) and 1-ethyl-3-(3-dimethylamino)propylcarbodiimide (9.6 mg) and the mixture stirred at room temperature. After 6 hours, the mixture was concentrated to half volume and applied to a small silica gel column for purification (ethyl acetate:hexane 1:6) to give 13 (3.5 mg).

MASS (FAB) 1015 (M+Li).

Partial $^1$H NMR δ: 5.18(d J=3.5 Hz, 1H); 4.87 (m, 1H); 3.79(m, 1H); 3.66(m, 1H); 3.40(s, 3H); 2.86(m, 1H).

EXAMPLE 13

1,14-Dihydroxy-12-[2'-4''-hydroxy-3''-methoxycyxlohexyl)-1'-methylethyl]-27-methyl-11,28-dioxa-4-azatricyclo[22.3.1.0$^{4,9}$]octacosane-2,3,10-trione To a solution the of product of Example 12 (4 mg in 200 μl of acetonitrile) was added 50 μl of a 2% solution of hydrogen fluoride in aqueous acetonitrile, and the mixture stirred at room temperature. After 1 hour, the reaction was quenched by addition of saturated sodium bicarbonate solution. This was extracted with ethyl acetate, dried by passage through a magnesium sulfate plug, and concentrated in vacuo to provide the monosilyl ether at C-10 (2 mg). This product was solvated at 0° C. with trifluoroacetic acid (400 μl) and stirred at low temperature. After 15 minutes, the stir bar was removed and the mixture concentrated in vacuo at 0° C. The concentrate was diluted with methylene chloride:ether (1:1) and the remaining acid quenched by addition of saturated sodium bicarbonate. The separated organics were dried by passage through a magnesium sulfate plug, and the concentrate purified by passage through a small silica gel column (ethyl acetate+1% methanol) to give 14 (0.8 mg).

MASS: (FAB) 672 (M+Li).

Partial $^1$H NMR δ: 5.15(brs, 1H); 5.04(m, 1H); 3.94(m, 1H); 3.76(m, 1H); 3.40(s, 3H); 2.95(m, 1H); 0.92(d J=7 Hz, 3H); 0.90(d J=3 Hz, 3H).

EXAMPLE 14

To a solution of 15 (3.26 g in 100 ml methylene chloride; prepared as described in: Gu, R. L.; Sih, C. J. *Tetrahedron Lett.* 1990, 31, 3287) was added 12 g methyl(triphenylphosphoranylidene) acetate and the mixture stirred at room temperature. After 16 hours, the mixture was concentrated in vacuo and the resulting oil purified by flash chromatography on silica gel (ethyl acetate:hexane 1:10) to give 16 (3.16 g).

Partial $^1$H NMR δ: 6.88(dd J=16, 7 Hz, 1H); 5.78(d J=16 Hz, 1H); 3.71 (s, 3H); 3.39 (s, 3H); 2.94(m, 1H).

EXAMPLE 15

To a solution of the product of Example 14 (3.16 g in 100 ml methylene chloride) was added diisobutylaluminum hydride (21.3 ml of a 1M solution in methylene chloride) and the mixture stirred at 0° C. After 30 minutes, the reaction is quenched by the slow addition of methanol and warmed to room temperature. To this was added 25 ml of saturated sodium sulfate solution and the slurry stirred rapidly for 2 hours then filtered over diatomaceous earth. The filtrate was washed with brine and the organic portion dried over magnesium sulfate. Purification of the concentrate by flash chromatography on silica gel (ethyl acetate:hexane 1:5) gave 17 (2.62 g).

Partial $^1$H NMR δ: 5.62(m, 2H); 4.07(brm, 2H); 3.39 (s, 3H); 2.92(m, 1H).

EXAMPLE 16

To a solution of oxalyl chloride (0.843 ml in 75 ml methylene chloride) at −78° C. was added 0.81 ml methyl sulfoxide and the mixture stirred for 15 min. To this, a solution of alcohol 17 (2.62 g in 6 ml methylene chloride) was added via syringe and the reaction stirred at −78° C. After 45 minutes, 4.9 ml of triethylamine was added and the mixture warmed to 0° C. The mixture was diluted with ether after 1 hour and extracted in turn with saturated sodium bicarbonate, saturated ammonium chloride, and brine, after which the organic portion was dried over magnesium sulfate. Purification of the concentrate by flash chromatography on silica gel (ethyl acetate:hexane 1:5) gave 18 (1.94 g).

Partial $^1$H NMR δ: 9.49(d J=9 Hz, 1H); 6.74(dd J=15, 7 Hz, 1H) 6.07(dd J=15, 9 Hz, 1H); 3.51(s, 3H); 2.98(m, 1H).

EXAMPLE 17

To a solution of the product of Example 16 (1.94 g in 60 ml ethanol) was added 100 mg of 10% palladium on carbon catalyst. The reaction flask was fitted with a hydrogen balloon, evacuated and recharged with hydrogen (3 times) and stirred at room temperature. After 1 hour, the mixture was filtered over diatomaceous earth, concentrated, and purified by passage through a small silica gel column (ethyl acetate:hexane 1:5) to give 19 (1.95 g).

Partial $^1$H NMR $\delta$: 9.76(t J=2 Hz, 1H); 3.39(s, 3H); 2.88(m, 1H); 2.43(td J=7, 2 Hz, 2H).

EXAMPLE 18

To a $-78°$ C. solution of the product of Example 17 (1.95 g in 70 ml toluene) was added 100 mg of powdered, 4A molecular sieves and diisopropyl-L-tartrate modified allylboronate (9.28 ml of a 20% toluene solution), and the mixture stirred at low temperature. After 15 minutes, an additional 10 ml of reagent were added. The mixture was quenched by the addition of saturated sodium bicarbonate solution after 1 hour reaction time. This was then diluted with ether, extracted, and dried over magnesium sulfate. Purification by flash chromatography on silica gel (ethyl acetate:hexane 1:5) gave 20 (1.54 g).

Partial $^1$H NMR $\delta$: 5.78(m, 1H); 5.16(brs, 1H); 5.08 (brs, 1H); 3.59 (m, 1H); 3.40 (s, 3H); 2.89(m, 1H).

EXAMPLE 19

To a solution of the product of Example 18 (1.54 g in 30 ml methylene chloride) was added diisopropylethylamine (3.15 ml) followed by benzyl chloromethyl ether (1.26 ml), and the mixture heated to reflux on a mantle. After 4 hours, the reaction mixture was cooled and poured into saturated sodium bicarbonate. The layers were separated and the aqueous portion extracted with ethyl acetate. The combined organics were washed with brine, dried over magnesium sulfate and concentrated in vacuo. Purification by flash chromatography on silica gel (ethyl acetate:hexane 1:5) gave 21 (1.65 g).

Partial $^1$H NMR $\delta$: 7.36(m, 5H); 5.84(m, 1H), 4.82(m, 2H); 4.75(d J=6 Hz, 2H); 3.68(m, 1H); 3.40(s, 3H).

EXAMPLE 20

To a solution of the product of Example 19 (0.76 g in 16 ml of a 1:1 mixture of methylene chloride:methanol) was added ca. 50 mg solid sodium bicarbonate and the mixture cooled to $-78°$ C. This was subjected to ozone gas until a blue-colored solution persisted. This was then decolorized at $-78°$ C. by bubbling nitrogen through the solution followed by addition of methyl sulfide (0.8 ml) and the mixture warmed to room temperature. After 2.5 hours, the mixture was diluted with ethyl acetate and washed successively with half-saturated sodium bicarbonate and brine. The organic portion was dried over magnesium sulfate concentrated in vacuo, and purified by flash chromatography on silica gel (ethyl acetate:hexane 1:5) gave 22 (560 mg).

Partial $^1$H NMR $\delta$: 9.79(t J=2 Hz, 1H); 7.33(m, 5H); 4.80(s, 2H); 4.60(s, 2H); 4.13(m, 1H); 3.38(s, 3H).

EXAMPLE 21

To a $-78°$ C. solution of the product of Example 20 (560 mg in 12 ml toluene) was added 50 mg of powdered, 4A molecular sieves and diisopropyl-L-tartrate modified allylboronate (1.72 ml of a 20% toluene solution), and the mixture stirred at low temperature. After 15 minutes, an additional 3.5 ml of reagent were added. The mixture was quenched by the addition of saturated sodium bicarbonate solution after 1 hour reaction time. This was then diluted with ether, extracted, and dried over magnesium sulfate. Purification by flash chromatography on silica gel (ethyl acetate:hexane 1:5) gave 23 (450 mg).

Partial $^1$H NMR $\delta$: 7.35(m, 5H); 5.87(m, 1H); 3.88(m, 2H); 3.41(s, 3H); 2.90(m, 1H); 2.25(brt J=5 Hz, 2H).

EXAMPLE 22

To a solution of the product of Example 5 (450 mg in 10 ml methylene chloride) was added 2,6-lutidine (260 $\mu$l) followed by tert-butyldimethylsilyl trifluoromethanesulfonate (246 $\mu$l) and the mixture stirred at room temperature. After 20 minutes, the reaction was quenched by the addition of saturated sodium bicarbonate. This was extracted 3 times with ethyl acetate, washed with brine, and the organic portion dried over magnesium sulfate. Purification of the concentrate by flash chromatography on silica gel (ethyl acetate:hexane 1:20) gave 24 (540 mg).

Partial $^1$H NMR $\delta$: 7.33(m, 5H); 5.84(m, 1H); 4.79(d J=6 Hz, 2H); 3.88(m, 1H); 3.72(m, 1H); 2.41(s, 3H).

EXAMPLE 23

To a solution of the product of Example 22 (150 mg in 3 ml of a 1:1 mixture of methylene chloride:methanol) was added ca. 20 mg solid sodium bicarbonate and the mixture cooled to $-78°$ C. This was subjected to ozone gas until a blue-colored solution persisted. This was then decolorized at $-78°$ C. by bubbling nitrogen through the solution followed by addition of methyl sulfide (500 $\mu$l) and the mixture warmed to room temperature. After 1 hour, the mixture was diluted with ethyl acetate and washed successively with half-saturated sodium bicarbonate and brine. The organic portion was dried over magnesium sulfate concentrated in vacuo to give crude 25 (147 mg).

Partial $^1$H NMR $\delta$: 9.79(t J=2 Hz, 1H); 7.35(m, 5H); 4.80(d J=6 Hz, 2H); 4.38(m, 1H); 3.70(m, 1H); 3.43(s, 3H); 2.90(m, 1H).

EXAMPLE 24

To a solution of the product of Example 23 (147 mg in 3 ml methylene chloride) was added 238 mg methyl (triphenylphosphoranylidene) acetate and the mixture stirred at room temperature. After 4 hours, the mixture was concentrated in vacuo and the resulting oil purified by flash chromatography on silica gel (ethyl acetate:hexane 1:10) to give 26 (118 mg).

Partial $^1$H NMR $\delta$: 7.33(m, 5H); 6.98(dt J=16, 8 Hz, 1H); 5.86(dd J=16, 3 Hz, 1H); 3.99(m, 1H); 3.74(s, 3H); 3.41(s, 3H); 2.89(m, 1H).

EXAMPLE 25

To a solution of the product of Example 24 (118 mg in 3 ml ethyl acetate) was added 10 mg of 20% palladium hydroxide on carbon catalyst. The reaction flask was fitted with a hydrogen balloon, evacuated and recharged with hydrogen (3 times) and stirred at room temperature. After 2 hours, the mixture was filtered over diatomaceous earth and concentrated in vacuo. This product was added directly (97 mg in 500 $\mu$l tetrahydrofuran) to a solution of the anion of methyl diethylphosphonate (prepared by mixing methyl diethylphosphonate, 160 mg, with tert-butyllithium, 1.23 ml of a 0.85M solution, in 2 ml of tetrahydrofuran at $-40°$ C. for 30 minutes). The reaction was quenched after 30 minutes by addition of saturated ammonium chloride and extracted with ether. The combined organics were dried over magnesium sulfate, and the concentrate purified by flash chromatography on silica gel (ethyl acetate:hexane (1:1)+1% methanol) to give 27 (82.6 mg).

Partial $^1$H NMR δ: 4.11(q J=7 Hz, 4H); 3.39(s, 3H); 3.05(d J=23 Hz, 2H); 1.33 (t J=7 Hz, 6H).

EXAMPLE 26

To a solution of β-keto phosphonate 27 (47.5 mg in 400 μl dry acetonitrile) was added lithium chloride (11.8 mg) and diisopropylethylamine (36.7 μl) and the suspension stirred at room temperature. After 15 minutes, a solution of aldehyde 28 (39.7 mg in 300 μl acetonitrile; 28 was prepared in an analogous manner to 10) was added. The reaction was quenched after 8 hours by addition of saturated ammonium chloride, extracted with ethyl acetate, and dried by passage through a magnesium sulfate plug. Purification of the concentrate by flash chromatography on silica gel (ethyl acetate:hexane 1:4) gave 29 (43 mg).

Partial $^1$H NMR δ: 7.36(s, 5H); 6.78(dt J=14, 6 Hz, 1H); 6.11(d J=14 Hz, 1H); 3.39(s, 3H); 0.78(d J=6 Hz, 3H).

EXAMPLE 27

To a solution of the product of Example 26 (43 mg in 1.5 ml ethyl acetate) was added 5 mg of 20% palladium hydroxide on carbon catalyst. The reaction flask was fitted with a hydrogen balloon, evacuated and recharged with hydrogen (3 times) and stirred at room temperature. After 30 minutes, the mixture was filtered over diatomaceous earth, concentrated, and purified by passage through a small silica gel column (ethyl acetate+1% acetic acid) to give 30 (27 mg).

Partial $^1$H NMR δ: 5.29(brs, 1H); 3.42(s, 3H); 2.92 (m, 1H); 0.78(d J=6 Hz, 3H).

EXAMPLE 28

To a solution of the seco-acid 30 (25 mg in 0.5 ml methylene chloride) was added a mixture of dimethylaminopyridine (16.3 mg) and 1-ethyl-3-(3-dimethylamino)propylcarbodiimide (26.1 mg) and the mixture stirred at room temperature. After 18 hours, the mixture was diluted with water and extracted with ethyl acetate. The organic portion was dried over magnesium sulfate and the concentrate purified by flash chromatography on silica gel (ethyl acetate:hexane (1:4)+1% methanol) to give 31 (12 mg).

MASS (FAB) 930 (M+Li).

Partial $^1$H NMR δ: 5.20(brs, 1H); 5.03(brm, 1H); 2.91 (m, 1H); 8.01(d, J=6 Hz, 3H).

EXAMPLE 29

To a solution of the product of Example 28 (9 mg in 600 μl of acetonitrile) was added 30 μl of a 2% solution of hydrogen fluoride in aqueous acetonitrile, and the mixture stirred at room temperature. After 45 minutes, the reaction was quenched by addition of saturated sodium bicarbonate solution. This was extracted with ethyl acetate, dried by passage through a magnesium sulfate plug, and the concentrate purified by flash chromatography on silica gel (ethyl acetate:methanol 10:1) to provide the mono-silyl ether at C-10 (4 mg). This product is solvated at 0° C. with trifluoroacetic acid (500 μl) and stirred at low temperature. After 15 minutes, the stir bar is removed and the mixture concentrated in vacuo at 0° C. The concentrate is then diluted with methylene chloride:ether (1:1) and the remaining acid quenched by addition of saturated sodium bicarbonate. The separated organics are dried by passage through a magnesium sulfate plug, and the concentrate purified by passage through a small silica gel column providing 32.

EXAMPLE 30

To a 0° C. solution of the product of Example 22 (111 mg in 2.0 ml ethylene glycol dimethyl ether) was added 9-borabicyclo[3.3.1]nonane (9-BBN, 716 μl of a 0.5M solution in tetrahydrofuran) and the mixture warmed to room temperature. After 15 minutes, an additional 500 μl of 9-BBN was added. The reaction was quenched after 1 hour by addition of half-saturated sodium bicarbonate, dilution with ether, and addition of 1 ml of 30% hydrogen peroxide. This was stirred vigorously for 30 minutes at which time the layers were separated and the aqueous portion washed with 10% sodium sulfite then extracted with ethyl acetate. The combined organics were dried over magnesium sulfate and concentrated in vacuo. Purification by flash chromatography on silica gel (ethyl acetate:hexane 1:3) gave 33 (64.1 mg).

Partial $^1$H NMR δ: 7.33(m, 5H); 4.78(d J=6 Hz, 2H); 3.41(s, 3H); 2.89(m, 1H).

EXAMPLE 31

To a solution of oxalyl chloride (38 μl in 1 ml methylene chloride) at −78° C. was added 37 μl methyl sulfoxide and the mixture stirred for 15 min. To this, a solution of the alcohol 33 (64 mg in 0.5 ml methylene chloride) was added via syringe and the reaction stirred at −78° C. After 45 minutes, 223 μl of triethylamine was added and the mixture warmed to 0° C. The mixture was diluted with ether after 1 hour and extracted in turn with saturated sodium bicarbonate, saturated ammonium chloride, and brine, after which the organic portion was dried over magnesium sulfate. Purification of the concentrate by flash chromatography on silica gel (ethyl acetate:hexane 1:4) gave 34 (48 mg).

Partial $^1$H NMR δ: 9.74(brd J=5 Hz, 1H); 7.35(s, 5H); 4.80(d J=6 Hz, 2H); 4.65(brs, 2H); 3.42(s, 3H); 2.91 (m, 1H).

EXAMPLE 32

To a solution of the product of Example 31 (78 mg in 0.8 ml methylene chloride) was added 123 mg methyl(triphenylphosphoranylidene) acetate and the mixture stirred at room temperature. After 16 hours, the mixture was concentrated in vacuo and the resulting oil purified by flash chromatography on silica gel (ethyl acetate:hexane 1:10) to give 35 (52 mg).

Partial $^1$H NMR δ: 7.34(m, 5H); 6.98(m, 1H); 5.83 (dd J=16, 3 Hz, 1H); 4.79 (d J=6 Hz, 2H); 4.64 (brs, 2H); 3.73(s, 3H); 3.41(s, 3H).

EXAMPLE 33

To a solution of the product of Example 32 (52 mg in 1.5 ml ethyl acetate) was added 10 mg of 20% palladium hydroxide on carbon catalyst. The reaction flask was fitted with a hydrogen balloon, evacuated and recharged with hydrogen (3 times) and stirred at room temperature. After 4 hours, the mixture was filtered over diatomaceous earth and concentrated in vacuo. This product was added directly (29 mg in 500 μl tetrahydrofuran) to a solution of the anion of methyl diethylphosphonate (prepared by mixing methyl diethylphosphonate, 47 mg, with tert-butyllithium, 360 μl of a 0.85M solution, in 1 ml of tetrahydrofuran at −40° C. for 30 minutes). The reaction is quenched after 30 minutes by addition of saturated ammonium chloride and extracted with ether. The combined organics were dried over magnesium sulfate, and the concentrate purified by flash chromatography on silica gel (ethyl acetate:hexane (1:1)+1% methanol) to give 36 (34 mg).

Partial $^1$H NMR $\delta$: 4.16(d q J=7, 7 Hz, 4H); 3.40 (s, 3H); 3.06 (d J=24 Hz, 2H); 2.64(t J=6 Hz, 2H); 1.34(t J=7 Hz, 6H).

EXAMPLE 34

To a solution of β-keto phosphonate 36 (34 mg in 400 μl dry acetonitrile) was added lithium chloride (8.4 mg) and diisopropylethylamine (26.2 μl) and the suspension stirred at room temperature. After 15 minutes, a solution of aldehyde 28 (25.4 mg in 500 μl acetonitrile; prepared in an analogous manner to 10 as described in *Tetrahedron Lett.* 1990, 31, 4845) was added. The reaction was quenched after 17 hours by addition of saturated ammonium chloride, extracted with ethyl acetate, and dried by passage through a magnesium sulfate plug. Purification of the concentrate by flash chromatography on silica gel (ethyl acetate:hexane 1:4) gave 37 (37 mg).

Partial $^1$H NMR $\delta$: 7.36(s, 5H); 6.78(dt J=14, 5 Hz, 1H); 6.11(d J=14 Hz, 1H); 3.40(s, 3H); 2.50(t J=7 Hz, 2H); 0.79(d J=6 Hz, 3H).

EXAMPLE 35

To a solution of the product of Example 34 (37 mg in 1.5 ml ethyl acetate) was added 5 mg of 20% palladium hydroxide on carbon catalyst. The reaction flask was fitted with a hydrogen balloon, evacuated and recharged with hydrogen (3 times) and stirred at room temperature. After 40 minutes, the mixture was filtered over diatomaceous earth, concentrated, and purified by passage through a small silica gel column (ethyl acetate+1% acetic acid) to give 38 (30 mg). $^1$H NMR was consistent with the desired structure.

EXAMPLE 36

To a solution of the seco-acid 38 (25 mg in 0.5 ml methylene chloride) was added a mixture of dimethylaminopyridine (21.1 mg) and 1-ethyl-3-(3-dimethylamino)propylcarbodiimide (33.9 mg) and the mixture stirred at room temperature. After 18 hours, the mixture was diluted with water and extracted with ethyl acetate. The organic portion was dried over magnesium sulfate and the concentrate purified by flash chromatography on silica gel (ethyl acetate:hexane (1:4)+1% methanol) to give 39 (11 mg).

Partial $^1$H NMR $\delta$: 5.21(brs, 1H); 5.03(brm, 1H); 3.42(s, 3H); 2.91(m, 1H); 0.81(d J=6 Hz, 3H).

EXAMPLE 37

To a solution of the product of Example 37 is added 30 μl of a 2% solution of hydrogen fluoride in aqueous acetonitrile, and the mixture stirred at room temperature. After 45 minutes, the reaction is quenched by addition of saturated sodium bicarbonate solution. This is extracted with ethyl acetate, dried by passage through a magnesium sulfate plug, and the concentrate is purified by flash chromatography on silica gel providing the mono-silyl ether at C-10. This product is solvated at 0° C. with trifluoroacetic acid (500 μl) and stirred at low temperature. After 15 minutes, the stir bar is removed and the mixture concentrated in vacuo at 0° C. The concentrate is then diluted with methylene chloride:ether (1:1) and the remaining acid quenched by addition of saturated sodium bicarbonate. The separated organics are dried by passage through a magnesium sulfate plug, and the concentrate purified by passage through a small silica gel column providing 40.

EXAMPLES 38-40

Utilizing the general procedures described in Examples 1 to 37, the following compounds of Formula I (wherein $R^1$, $R^2$, $R^3$, $R^7$ and $R^8$ are hydrogen) are prepared from the appropriately substituted starting materials and reagents.

| EXAMPLE NO. | X | $R^4$ | $R^5$ |
|---|---|---|---|
| 38 | —CH$_2$— | —CH$_2$CH$_2$CH$_3$ | —OH |
| 39 | —CH$_2$CH$_2$— | —CH$_2$C$_6$H$_5$ | —OH |
| 40 | —CH$_2$CH$_2$CH$_2$— | —CH$_2$C$_6$H$_5$ | —OH |

EXAMPLE 41

Antagonism Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. For antagonist activity dilutions of compounds were cultured with L-679,934 (as a standard) at a concentration of 1.2 nM, a concentration which inhibits T cell proliferation by 100%.

The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%.

A selection of compounds were tested according to the previous procedure. The concentration of compound required reverse the inhibition obtained by L-679,934 (the standard) alone, by 50% was measured, and the results were as follows.

The title compound of the following Example exhibited an $ED_{50} < 5 \times 10^{-6}$ (M): 13.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

[structure]

or a pharmaceutically acceptable salt thereof, wherein:
X is selected from:

[structures]

or forms a single bond;
W is O, (H, OH), or (H, H);
Y is O, (H, OH, or (H, H);
$R^1$ and $R^2$ are hydrogen or taken together form a double bond;
$R^3$ is hydrogen or methyl;
$R^4$ is selected from:
  (1) hydrogen, or
  (2) $C_{1-6}$ alkyl, unsubstituted or substituted with one or more of:
    (a) $C_{1-6}$ alkoxy,
    (b) phenyl, unsubstituted or substituted with $C_{1-6}$ alkyl,
$R^5$ is hydrogen or hydroxy;
$R^6$ is selected from:
  (1) hydrogen;
  (2) $C_{1-6}$ alkyl, unsubstituted or substituted with one or more of:
    (a) $C_{1-6}$ alkoxy,
    (b) phenyl, unsubstituted or substituted with $C_{1-6}$ alkyl,
  (3) $C_{2-6}$ alkenyl; and
$R^7$ and $R^8$ are hydrogen or taken together from a double bond.

2. The compound of claim 1 wherein:
X is selected from:

[structures]

W is (H, H);
Y is O;
$R^1$ and $R^2$ are hydrogen;
$R^3$ is hydrogen or methyl;
$R^4$ is selected from:
  (1) hydrogen, or
  (2) unsubstituted $C_{1-6}$ alkyl;
$R^5$ is hydrogen or hydroxy;
$R^6$ is hydrogen; and
$R^7$ and $R^8$ are hydrogen.

3. The compound of claim 2 which is:

[structure]

4. The compound of claim 2 which is:

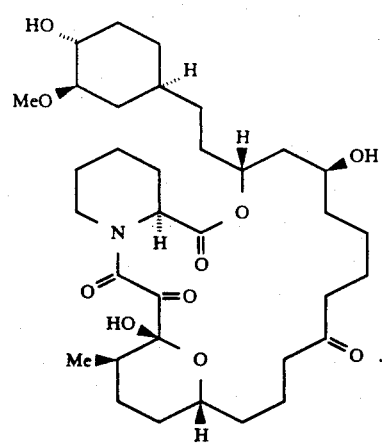

5. The compound of claim 2 which is:

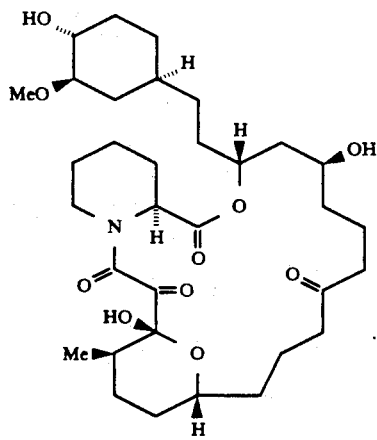

6. A pharmaceutical composition for the treatment of immunoregulatory disorders or diseases comprising a pharmaceutical carrier and a therapeutically effective amount of compound of claim 1.

7. A pharmaceutical composition for the treatment or resistance to transplantation comprising a pharmaceutical carrier and a therapeutically effective amount of compound of claim 1.

8. A pharmaceutical composition for the topical treatment of inflammatory and hyperproliferative skin diseases and or cutaneous manifestations of immunologically-mediated illnesses comprising a pharmaceutical carrier and a therapeutically effective amount of compound of claim 1.

9. A method for the treatment of immunoregulatory disorders or diseases comprising the administration to a mammalian species in need of such treatment an effective amount of a compound of claim 1.

10. A method for the treatment of resistance to transplantation comprising the administration to a mammalian species in need of such treatment and effective amount of a compound of claim 1.

11. A method for the topical treatment of inflammatory and hyperproliferative skin diseases and or cutaneous manifestations of immunologically-mediated illnesses comprising the administration to a mammalian species in need of such treatment an effective amount of a compound of claim 1.

12. A method for the antagonism of the activity of an FK-506-type immunosuppressant comprising the administration to a mammalian species in need of such antagonism of an effective amount of the compound of claim 1.

13. A method for the modification of treatment with an FK-506-type immunosuppressant comprising the administration to a mammalian species in need of such modification of an effective amount of the compound of claim 1.

* * * * *